US011583001B2

(12) United States Patent
Spencer et al.

(10) Patent No.: US 11,583,001 B2
(45) Date of Patent: Feb. 21, 2023

(54) AEROSOL DELIVERY SYSTEM

(71) Applicant: Nicoventures Trading Limited, London (GB)

(72) Inventors: Alfred Vincent Spencer, London (GB); Kevin David Blick, London (GB); Julie Jenson Bennett, London (GB); Connor Bruton, London (GB); Anna Koc, London (GB)

(73) Assignee: Nicoventures Trading Limited, London (GB)

( * ) Notice: Subject to any disclaimer, the term of this patent is extended or adjusted under 35 U.S.C. 154(b) by 491 days.

(21) Appl. No.: 16/497,264

(22) PCT Filed: Mar. 19, 2018

(86) PCT No.: PCT/GB2018/050706
§ 371 (c)(1),
(2) Date: Sep. 24, 2019

(87) PCT Pub. No.: WO2018/178628
PCT Pub. Date: Oct. 4, 2018

(65) Prior Publication Data
US 2020/0376208 A1 Dec. 3, 2020

(30) Foreign Application Priority Data
Mar. 29, 2017 (GB) ..................................... 1704999

(51) Int. Cl.
*A24F 40/30* (2020.01)
*A61M 11/04* (2006.01)
(Continued)

(52) U.S. Cl.
CPC .............. *A24F 40/30* (2020.01); *A24F 40/40* (2020.01); *A61M 11/042* (2014.02);
(Continued)

(58) Field of Classification Search
CPC .......... A24F 40/40; A24F 40/30; A24F 40/10; A24F 40/50; A61M 11/042; A61M 15/0003; A61M 15/06; A61M 2205/8206
(Continued)

(56) References Cited

U.S. PATENT DOCUMENTS 5,186,166 A * 2/1993 Riggs .................... B05B 7/0012 128/207.14
5,437,267 A * 8/1995 Weinstein .............. A62B 23/06 128/207.18
(Continued)

FOREIGN PATENT DOCUMENTS

AU 2013237685 A1 10/2013
CN 204032369 2/2014
(Continued)

OTHER PUBLICATIONS

Great Britain Search Report, application No. GB 1704999.0, filed dated Jun. 20, 2017, 4 pages.
(Continued)

*Primary Examiner* — Abdullah A Riyami
*Assistant Examiner* — Vladimir Imas
(74) *Attorney, Agent, or Firm* — Patterson Thuente, P.A.

(57) ABSTRACT

An aerosol delivery system including a first engagement mechanism, a first power supply, and a first vaporizer, wherein the first vaporizer is arranged to selectively receive power from the first power supply to generate a first aerosol from a first aerosol precursor material for user inhalation; and a second aerosol delivery device including a second engagement mechanism, a second power supply, and a second vaporizer, wherein the second vaporizer is arranged to selectively receive power from the second power supply to generate a second aerosol from a second aerosol precursor material for user inhalation; wherein the first engagement
(Continued)

mechanism of the first aerosol delivery device and the second engagement mechanism of the second aerosol delivery device are arranged to releasably co-engage with one another to selectively couple the first aerosol delivery device to the second aerosol delivery device so the first aerosol delivery device and the second aerosol delivery device may be used together to deliver the first and second aerosols to a single user when they are coupled together and may be used independently to deliver the first and second aerosols to different users when they are not coupled together.

17 Claims, 4 Drawing Sheets

(51) Int. Cl.
*A61M 15/00* (2006.01)
*A24F 40/40* (2020.01)
*A61M 15/06* (2006.01)
*A24F 40/10* (2020.01)
*A24F 40/50* (2020.01)

(52) U.S. Cl.
CPC ........ *A61M 15/0003* (2014.02); *A61M 15/06* (2013.01); *A24F 40/10* (2020.01); *A24F 40/50* (2020.01); *A61M 2205/8206* (2013.01)

(58) Field of Classification Search
USPC ...................................................... 128/200.14
See application file for complete search history.

(56) References Cited

U.S. PATENT DOCUMENTS

| | | | | |
|---|---|---|---|---|
| 5,603,314 | A * | 2/1997 | Bono | A61M 11/002 128/205.12 |
| 6,230,703 | B1 * | 5/2001 | Bono | A61M 11/002 128/200.14 |
| 8,757,147 | B2 * | 6/2014 | Terry | A61M 11/042 131/273 |
| 9,585,981 | B2 * | 3/2017 | Wynalda, Jr. | F22B 1/284 |
| 9,763,478 | B2 * | 9/2017 | Cameron | A24F 40/65 |
| 9,936,738 | B2 * | 4/2018 | Cameron | H05B 3/12 |
| 10,039,320 | B2 * | 8/2018 | Cameron | A24F 40/30 |
| 10,653,185 | B2 * | 5/2020 | Mazur | A61M 15/06 |
| 10,945,463 | B2 * | 3/2021 | Dickens | A61M 11/042 |
| 2011/0265806 | A1 * | 11/2011 | Alarcon | A24F 40/485 131/273 |
| 2014/0261486 | A1 | 9/2014 | Potter et al. | |
| 2015/0027459 | A1 | 1/2015 | Collett et al. | |
| 2015/0296879 | A1 | 10/2015 | Emarlou | |
| 2016/0192709 | A1 | 7/2016 | Liu | |
| 2016/0213866 | A1 * | 7/2016 | Tan | A61M 15/0085 |
| 2016/0262454 | A1 | 9/2016 | Sears et al. | |
| 2016/0262456 | A1 | 9/2016 | Borkovec et al. | |
| 2016/0331026 | A1 | 11/2016 | Cameron | |
| 2016/0345621 | A1 * | 12/2016 | Li | A24B 15/167 |
| 2017/0079322 | A1 * | 3/2017 | Li | A24B 15/16 |
| 2017/0196265 | A1 | 7/2017 | Liu | |
| 2018/0160733 | A1 * | 6/2018 | Leadley | H05B 3/44 |
| 2018/0184711 | A1 * | 7/2018 | Dickens | A24F 40/40 |
| 2018/0271155 | A1 * | 9/2018 | Baker | A24F 40/65 |
| 2020/0376208 | A1 * | 12/2020 | Spencer | A61M 15/0003 |
| 2020/0383378 | A1 * | 12/2020 | Moloney | H05B 1/0227 |
| 2021/0059301 | A1 * | 3/2021 | Hejazi | A61M 11/003 |
| 2021/0106774 | A1 * | 4/2021 | Ezeoke | A24F 40/51 |
| 2021/0298355 | A1 * | 9/2021 | Xing | A24F 40/10 |
| 2022/0061394 | A1 * | 3/2022 | Hejazi | A24F 40/48 |
| 2022/0117298 | A1 * | 4/2022 | Lukan | A24F 40/60 |

FOREIGN PATENT DOCUMENTS

| | | | |
|---|---|---|---|
| CN | 204499476 | U | 7/2015 |
| CN | 204579888 | | 8/2015 |
| CN | 204969454 | U | 1/2016 |
| CN | 105962416 | A | 9/2016 |
| CN | 205547367 | U | 9/2016 |
| CN | 106061300 | A | 10/2016 |
| CN | 106455696 | A | 2/2017 |
| EA | 019736 | B1 | 5/2014 |
| JP | 2014528718 | A | 10/2014 |
| JP | 2015513970 | A | 5/2015 |
| JP | 2016510994 | A | 4/2016 |
| RU | 2596108 | C1 | 8/2016 |
| WO | WO-2013152873 | A1 | 10/2013 |
| WO | WO-2014012906 | A1 | 1/2014 |
| WO | WO-2014032276 | A1 | 3/2014 |
| WO | WO-2015131374 | A1 | 9/2015 |
| WO | WO-2016092261 | A1 | 6/2016 |
| WO | WO-2016127473 | A1 | 8/2016 |
| WO | WO2016183573 | | 11/2016 |
| WO | WO2017001818 | | 1/2017 |

OTHER PUBLICATIONS

International Search Report and Written Opinion, application No. PCT/GB2018/050706, dated May 14, 2018, 12 pages.
Second Written Opinion, application No. PCT/GB2018/050706,, dated Mar. 8, 2019, 6 pages.
International Preliminary Report on Patentability, application No. PCT/GB2018/050706, dated Aug. 1, 2019, 6 pages.
Donglai Z., et al., "Electronic Cigarette," Aug. 31, 2015, Yunnan University Press, 1 page.
Office Action and Search Report dated Apr. 6, 2022 for Chinese Application No. 201880035589.5, 7 pages.
Office Action For Chinese Application No. 2018800355895, dated Sep. 24, 2021, 20 pages.
Office Action dated Feb. 2, 2021 for Japanese Application No. 2019-552903, 5 pages.

* cited by examiner

AEROSOL DELIVERY SYSTEM

PRIORITY CLAIM

The present application is a National Phase entry of PCT Application No. PCT/GB2018/050706, filed Mar. 19, 2018, which claims priority from GB Patent Application No. 1704999.0, filed Mar. 29, 2017, which is hereby fully incorporated herein by reference.

FIELD

The present disclosure relates to aerosol delivery systems such as electronic nicotine delivery systems (e.g. electronic cigarettes and the like).

BACKGROUND

Aerosol delivery systems such as electronic cigarettes (e-cigarettes) generally contain an aerosol precursor material or aerosol source, such as a reservoir of a source liquid containing a formulation, typically including nicotine and often flavorants, or a solid material such as a tobacco-based product, from which an aerosol is generated for inhalation by a user, for example through atomization/heat vaporization. Thus, an aerosol delivery system will typically comprise an aerosol generation chamber containing an atomizer or vaporizer, e.g. a heating element, arranged to atomize (or vaporize) a portion of precursor material to generate an aerosol in the aerosol generation chamber. As a user inhales on the device through a mouthpiece and electrical power is supplied to the atomizer, air is drawn into the device through inlet holes and into the aerosol generation chamber where the air mixes with the atomized precursor material to form an aerosol. There is a flow path connecting between the aerosol generation chamber and an opening in the mouthpiece so the incoming air drawn through the aerosol generation chamber continues along the flow path to the mouthpiece opening, carrying some of the aerosol with it, and out through the mouthpiece opening for inhalation by the user.

Aerosol delivery systems may comprise a modular assembly including both reusable and replaceable cartridge parts. Typically a cartridge part will comprise the consumable aerosol precursor material and the atomizer, while a reusable device part will comprise longer-life items, such as a rechargeable battery, device control circuitry, activation sensors and user interface features. The reusable part may also be referred to as a control unit or battery section and replaceable cartridge parts may also be referred to as cartomizers.

Cartomizers are electrically and mechanically coupled to a control unit for use, for example using a screw thread or bayonet fixing with appropriately engaging electrical contacts. When the aerosol precursor material in a cartomizer is exhausted, or the user wishes to switch to a different cartomizer having a different aerosol precursor material, a cartomizer may be removed from the control unit and a replacement cartomizer attached in its place.

Switching between cartomizers can be inconvenient for a user, especially if a user is repeatedly switching between two or more flavors on a regular basis as this requires disassembly and reassembly of the electronic cigarette by splitting the aerosol delivery device into its modular components to switch flavor. Electronic cigarettes have been thus been proposed with different precursor/source material arranged in a single device to provide different aerosols (e.g., having different flavors) to a user inhaling on the mouthpiece, either automatically or in response to user selection. The sources of material to be vaporized are typically located within the electronic cigarette and so still requires disassembly and reassembly of the electronic cigarette if the user wishes to switch to using a further source material or to lend one of the sources of material to another user.

Various approaches are described herein which seek to help address some of these issues.

SUMMARY

According to a first aspect of certain embodiments there is provided an aerosol delivery system including a first aerosol delivery device comprising a first engagement mechanism, a first power supply, and a first vaporizer, wherein the first vaporizer is arranged to selectively receive power from the first power supply to generate a first aerosol from a first aerosol precursor material for user inhalation; and a second aerosol delivery device comprising a second engagement mechanism, a second power supply, and a second vaporizer, wherein the second vaporizer is arranged to selectively receive power from the second power supply to generate a second aerosol from a second aerosol precursor material for user inhalation; wherein the first engagement mechanism of the first aerosol delivery device and the second engagement mechanism of the second aerosol delivery device are arranged to releasably co-engage with one another to selectively couple the first aerosol delivery device to the second aerosol delivery device so the first aerosol delivery device and the second aerosol delivery device may be used together to deliver the first and second aerosols to a single user when they are coupled together and may be used independently to deliver the first and second aerosols to different users when they are not coupled together.

According to a second aspect of certain embodiments there is provided an aerosol delivery device comprising: a power supply; a vaporizer arranged to selectively receive power from the power supply to generate an aerosol from an aerosol precursor material for user inhalation; and an engagement mechanism for releasably co-engaging the aerosol delivery device with a further aerosol delivery device arranged to generate a further aerosol for user inhalation so the aerosol delivery device and the further aerosol delivery device may be used together to deliver aerosol to a single user when they are coupled together and the aerosol delivery device may be used independently of the other aerosol delivery device when the aerosol delivery device is not coupled to the other aerosol delivery device.

According to a third aspect of certain embodiments there is provided an aerosol delivery system including first aerosol delivery means comprising first engagement means, first power supply means, and first vaporizing means, wherein the first vaporizing means is arranged to selectively receive power from the first power supply means to generate a first aerosol from a first aerosol precursor material for user inhalation; and second aerosol delivery means comprising second engagement means, second power supply means, and second vaporizing means, wherein the second vaporizing means is arranged to selectively receive power from the second power supply means to generate a second aerosol from a second aerosol precursor material for user inhalation; wherein the first engagement means of the first aerosol delivery means and the second engagement means of the second aerosol delivery means are arranged to releasably co-engage with one another to selectively couple the first aerosol delivery means to the second aerosol delivery means so the first aerosol delivery means and the second aerosol delivery means may be used together to deliver the first and second aerosols to a single user when they are coupled together and may be used independently to deliver the first and second aerosols to different users when they are not coupled together.

It will be appreciated that features and aspects of the disclosure described above in relation to the first and other aspects of the disclosure are equally applicable to, and may be combined with, embodiments of the invention according to other aspects of the disclosure as appropriate, and not just in the specific combinations described above.

BRIEF DESCRIPTION OF THE DRAWINGS

Embodiments of the disclosure will now be described, by way of example only, with reference to the accompanying drawings, in which.

DETAILED DESCRIPTION

Aspects and features of certain examples and embodiments are discussed/described herein. Some aspects and features of certain examples and embodiments may be implemented conventionally and these are not discussed/described in detail in the interests of brevity. It will thus be appreciated that aspects and features of apparatus and methods discussed herein which are not described in detail may be implemented in accordance with any conventional techniques for implementing such aspects and features.

The present disclosure relates to aerosol delivery systems, which may also be referred to as aerosol provision systems, such as e-cigarettes. Throughout the following description the term "e-cigarette" or "electronic cigarette" may sometimes be used; however, it will be appreciated this term may be used interchangeably with aerosol delivery system and electronic aerosol delivery system. Furthermore, and as is common in the technical field, the terms "vapor" and "aerosol", and related terms such as "vaporize" and "aerosolize", may also be used interchangeably.

The present disclosure provides an aerosol delivery system which includes at least two aerosol delivery devices. Each aerosol delivery device is provided with components required to generate aerosol from a respective aerosol precursor material that can be located within the aerosol delivery devices and to subsequently deliver aerosol generated from this precursor material to a user. The present disclosure provides a system whereby aerosol delivery devices comprise respective engagement mechanisms that can be co-engaged with one another to selectively couple together the aerosol delivery devices such that, during use, the first and second aerosol delivery devices can deliver the first and second aerosols to a single user. For instance, the user can inhale on mouthpiece openings of both aerosol delivery devices simultaneously to receive a mixture of the aerosols separately generated by the coupled aerosol delivery devices. The engagement mechanism may be mechanical or magnetic in nature and provides a sufficiently strong coupling to prevent separation of the aerosol delivery devices during normal use (i.e., when inhaling on the mouthpiece openings simultaneously) but enables the aerosol delivery devices to be separated under (deliberate) application of a separation force to the aerosol delivery devices. In an uncoupled state, each aerosol delivery device is configured to generate aerosol independently of the other aerosol delivery device—that is, each aerosol delivery device is capable of independent use. In this way, switching of the aerosol delivery devices, e.g., to provide a different flavor or aerosol precursor material combinations, can be performed intuitively and easily without disassembling individual aerosol delivery devices.

Figure 1:
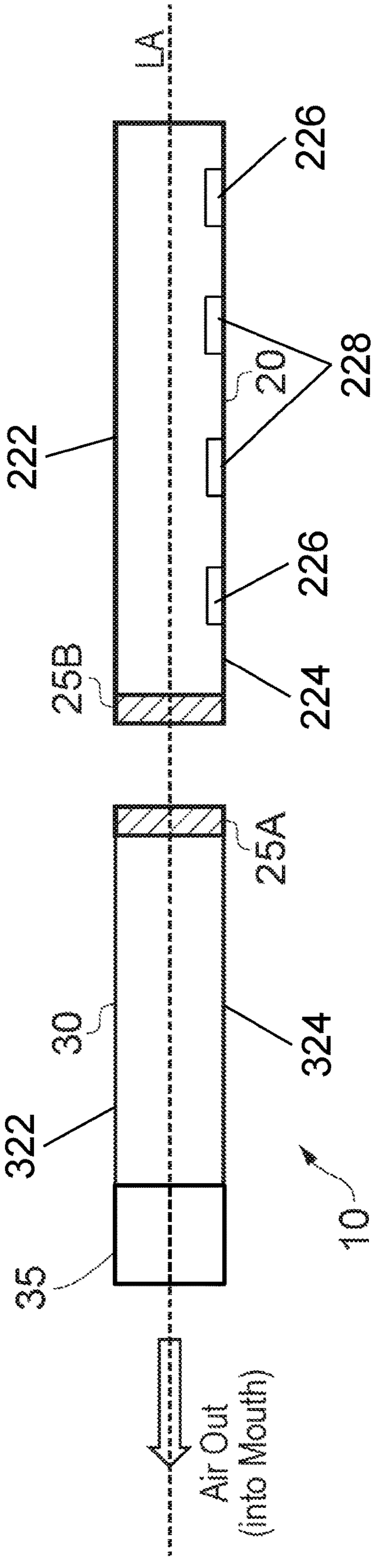
FIG. 1 schematically represents an aerosol delivery device having an uncoupled cartomizer and control unit in cross-section along a longitudinal axis thereof for use in an aerosol delivery system in accordance with an embodiment of the disclosure.

FIG. 1 is a schematic diagram of an aerosol delivery device 10 in accordance with some embodiments of the present disclosure. The aerosol delivery device 10 has a generally cuboidal shape (see also FIG. 4), extending along a longitudinal axis indicated by dashed line LA, and comprises two main components, namely a control unit 20 and a cartomizer 30.

The cartomizer 30 includes an internal chamber containing a reservoir of liquid formulation including nicotine (or more generally a precursor material), a heater (or more generally a vaporizer/atomizer), and a mouthpiece end 35. The cartomizer 30 may further include a wick or similar facility to transport a small amount of the liquid formulation from the reservoir to the heater. The control unit 20 includes a re-chargeable battery as a power supply/source to provide power to the aerosol delivery device 10 and a circuit board for generally controlling the aerosol delivery device 10. When the heater receives power from the battery, as controlled by the circuit board, the heater atomizes (heats) the nicotine and this aerosol (vapor) is then inhaled by a user through the mouthpiece end 35, specifically through one or more openings 352 therein (see FIGS. 3 and 4).

The control unit 20 and cartomizer 30 are detachable from one another by separating in a direction parallel to the longitudinal axis LA, as shown in FIG. 1, but are joined together when the device 10 is in use by a connection, indicated schematically in FIG. 1 as 25A and 25B, to provide mechanical and electrical connectivity between the control unit 20 and the cartomizer 30. The electrical connector on the control unit 20 that is used to connect to the cartomizer 30 may also serve as a socket for connecting a charging device (not shown) when the control unit 20 is detached from the cartomizer 30, or alternatively, the control unit 20 may be provided with a dedicated charging port (such as a USB port) at one end thereof, e.g., the end opposite the end configured to couple to the cartomizer 30. The cartomizer 30 may be detached from the control unit 20 and disposed of when the supply of nicotine is exhausted (and replaced with another cartomizer if so desired).

FIG. 1 schematically indicates various surfaces of the cartomizer 30 and control unit 20. Specifically, the control unit 20 has an upper/top surface 222 and a lower/bottom surface 224. The lower surface 224 is the surface of the control unit 20 directly opposite the upper surface 222. Equally, the cartomizer 30 has an upper surface 322 and a lower surface 324. The lower surface 324 is the surface of the cartomizer 30 directly opposite the upper surface 322. It will be appreciated that this terminology, i.e., upper/lower or equivalent, is used purely for convenience of explanation and is not intended to suggest a particular orientation of the aerosol delivery device 10 should be adopted in normal use. In some cases, and as will become apparent later, the aerosol delivery device 10 may be rotated about the longitudinal axis LA such that the upper surfaces 222 and 322 face downwards, i.e., the orientation of the surfaces as seen in FIG. 1 is reversed.

FIG. 1 (and also FIG. 3 described later) represents the mouthpiece end 35 of the cartomizer 30 as a separate box. It should be understood that this representation is not meant to signify that the mouthpiece end 35 is a separate piece/component of the cartomizer 30, but rather a region of the cartomizer 30 which engages with the user's lips when the user desires to inhale aerosol generated by the device 10 with the mouthpiece end 35 of the cartomizer 30 being modified in some way to allow aerosol to pass from inside the cartomizer 30 to outside, e.g., by one or more openings 352. Equally, it should be understood that in alternative implementations the mouthpiece end 35 is provided as a separate component that is attachable to and detectable from the main body of the cartomizer 30. In these alternative implementations, the main body of the cartomizer (which contains the reservoir for storing the aerosol precursor) can be replaced or switched with another main body, e.g., when the reservoir is empty or to change flavors of the aerosol generated. Retaining the mouthpiece end 35 may be advantageous when switching aerosol delivery devices between different users for reasons of hygiene.

As also seen in FIG. 1, the control unit 20 in this implementation comprises two magnetic portions 226 spaced from each other along the longitudinal axis LA. The magnetic portions 226 form a first engagement mechanism arranged to co-engage with a second engagement mechanism of a second aerosol delivery to selectively magnetically couple the aerosol delivery device 10 to the second aerosol delivery device. The magnetic portions 226 can have the magnetic poles aligned in any desired orientation. That is, the magnetic portions can be arranged to either have the magnetic poles in an upper/lower arrangement (e.g., south pole facing toward the upper surface 222 and north pole facing toward the lower surface 224) or in a left/right arrangement (e.g., south pole facing toward the connection 25B and north pole facing toward the opposite end of the control unit 20). The magnetic coupling will be described in more detail below.

Between the magnetic portions 226 are provided two electrical contacts 228 which are configured to provide positive and negative electrical terminals respectively. The electrical contacts 228 are connected to a controller within the control unit 20 and the power source. In essence, the electrical contacts 228 enable power and/or control signals to be passed to/from the power source or controller respectively from/to a second aerosol delivery device magnetically coupled to the aerosol delivery device 10 by the magnetic portions 226. That is, the power and/or control signals can be passed between coupled aerosol delivery devices using the electrical coupling. The electrical coupling will be described in more detail below.

It should be appreciated that the magnetic portions 226 and electrical contacts 228 are not shown to scale in FIG. 1. In FIG. 1, these portions 226 and contacts 228 are schematically represented as protruding into the body of the control unit 20 and being flush with the lower surface 224 thereof. However, the magnetic portions 226 and electrical contacts 228 in other embodiments can be constructed as strips applied to/provided on the surface 224 of the body of the control unit 20 and protrude by an amount equal to the thickness of the strip from the surface 224.

Figure 2:
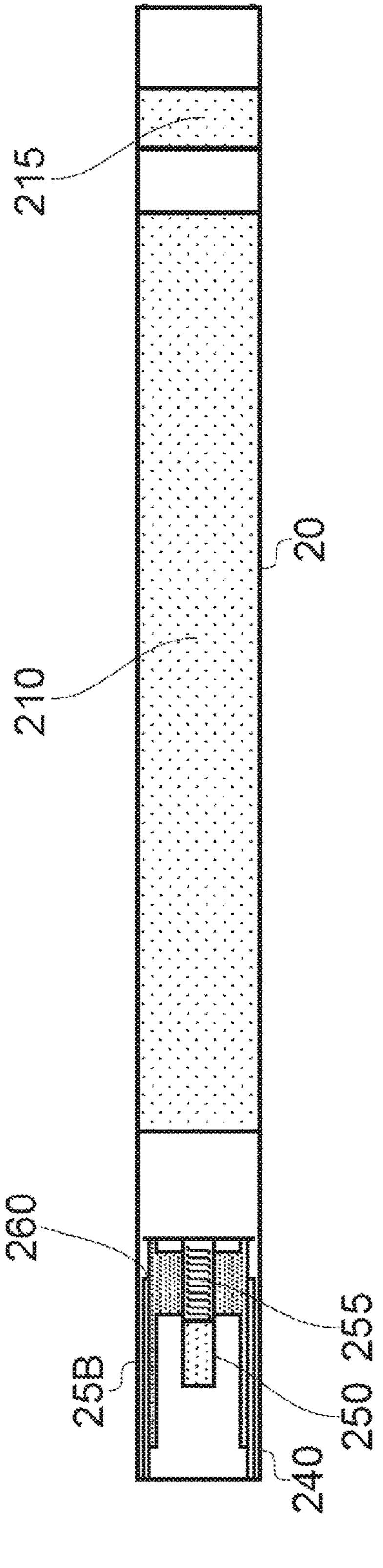
FIG. 2 schematically represents the control unit of FIG. 1 in cross-section along a longitudinal axis thereof.
Figure 3:
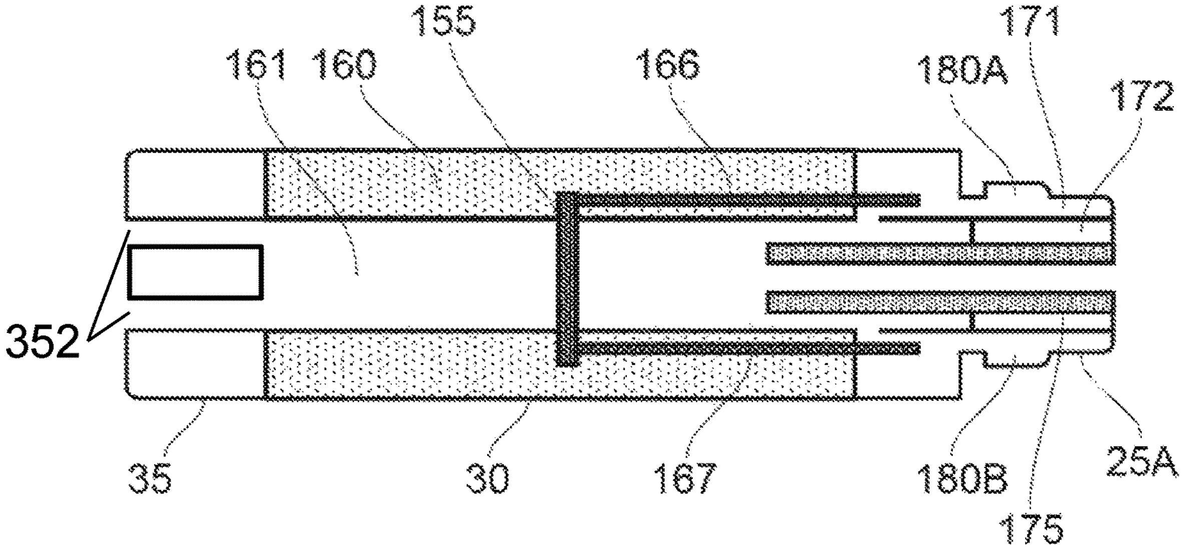
FIG. 3 schematically represents the cartomizer of FIG. 1 in cross-section along a longitudinal axis thereof.

FIGS. 2 and 3 provide schematic diagrams of the control unit 20 and cartomizer 30 respectively of the aerosol delivery device of FIG. 1. Note that various components and details, e.g. such as wiring and more complex shaping, have been omitted from FIGS. 2 and 3 for reasons of clarity in addition to the magnetic portions 226 and electrical contacts 228.

As shown in FIG. 2, the control unit 20 includes, as the power source, a re-chargeable battery or cell 210 for powering the aerosol delivery device 10, as well as a chip, such as a (micro)controller for controlling the aerosol delivery device 10. The controller is attached to a small printed circuit board (PCB) 215 that also includes a sensor unit. If a user inhales on the mouthpiece end 35, air is drawn into the aerosol delivery device 10 through one or more air inlet holes (not shown in FIGS. 1 and 2). The sensor unit detects this airflow, and in response to such a detection, the controller provides power from the battery 210 to the heater 155 in the cartomizer 30.

As shown in FIG. 3, the cartomizer 30 includes an air passage 161 extending along the central (longitudinal) axis of the cartomizer 30 from the mouthpiece end 35 to the connector 25A for joining the cartomizer to the control unit 20. A reservoir 160 of nicotine-containing liquid is provided around the air passage 161. This reservoir 160 may be implemented, for example, by providing cotton or foam soaked in the liquid. The cartomizer also includes a heater 155 in the form of a coil of wire for heating liquid from reservoir 160 to generate aerosol to flow through air passage 161 and out through mouthpiece end 35. The mouthpiece end 35 is provided with two openings 352 fluidly connected to the air passage 161 through which aerosol can be passed to the user's lungs. The heater is powered through lines 166 and 167, which are in turn connected to opposing polarities (positive and negative, or vice versa) of the battery 210 via connector 25A (the details of the wiring between the power lines 166 and 167 and connector 25A are omitted from FIG. 3).

One end of the control unit 20 provides a connector 25B for joining the control unit 20 to the connector 25A of the cartomizer 30. The connectors 25A and 25B provide mechanical and electrical connectivity between the control unit 20 and the cartomizer 30. The connector 25B includes two electrical terminals, an outer electrode 240 and an inner electrode 250, which are separated by insulator 260. The connector 25A likewise includes an inner electrode 175 and an outer electrode 171, separated by insulator 172. The insulator 172 is surrounded by the outer electrode 171. The outer electrodes 171 and 240 and inner electrodes 175 and 250 are formed from an electrically conductive material, such as metal, or are coated/plated with a conductive material (e.g., silver-plated) while the insulators 171 and 260 are formed from a non-conductive material, such as plastic, rubber, silicone, or any other suitable material. When the cartomizer 30 is connected to the control unit 20, the inner electrode 175 and the outer electrode 171 of the cartomizer 30 engage the inner electrode 250 and the outer electrode 240 respectively of the control unit 20. The inner electrode 250 is mounted on a coil spring 255 so that the inner electrode 175 pushes against the inner electrode 250 to compress the coil spring 255, thereby helping to ensure good electrical contact when the cartomizer 30 is connected to the control unit 20.

The cartomizer connector 25A is provided with two lugs or tabs 180A, 180B, which extend in opposite directions away from the longitudinal axis of the cartomizer 30. These tabs 180A, 180B are used to provide a mechanical connection between the cartomizer 30 and the control unit 20. The tabs 180A, 180B in this implementation flexibly engage with corresponding recesses (not shown) in the control unit 20 to provide a snap-fit type engagement to couple the cartomizer 30 to the control unit 20 when the cartomizer 30 is forced toward the control unit 20 along the longitudinal axis LA. In this regard, the tabs 180A, 180B are compressible in a direction towards the longitudinal axis LA to enable the cartomizer 30 to be inserted into the control unit 20 and are shaped so as to resist separation of the cartomizer 30 and control unit 20 when the tabs 180A, 180B are engaged with the corresponding recesses. The snap-fit engagement provides a secure and robust connection between the cartomizer 30 and the control unit 20 so that the cartomizer 30 and control unit 20 are held in a fixed position relative to one another, without wobble or flexing, and the likelihood of any accidental disconnection is very small. Other snap-fit engagement mechanisms may be provided that are constructed in an alternative manner to that described above. Moreover, it will be appreciated that other embodiments may use a different form of connection between the control unit 20 and the cartomizer 30, such as a bayonet or a screw connection.

As mentioned above, the cartomizer 30 is generally disposed of once the liquid reservoir 160 has been depleted, and a new cartomizer is purchased and installed. Alternatively, the cartomizer 30 may be refilled with a new liquid and replaced. In either case the cartomizer 30 is generally removed from the control unit 20.

Figure 4:
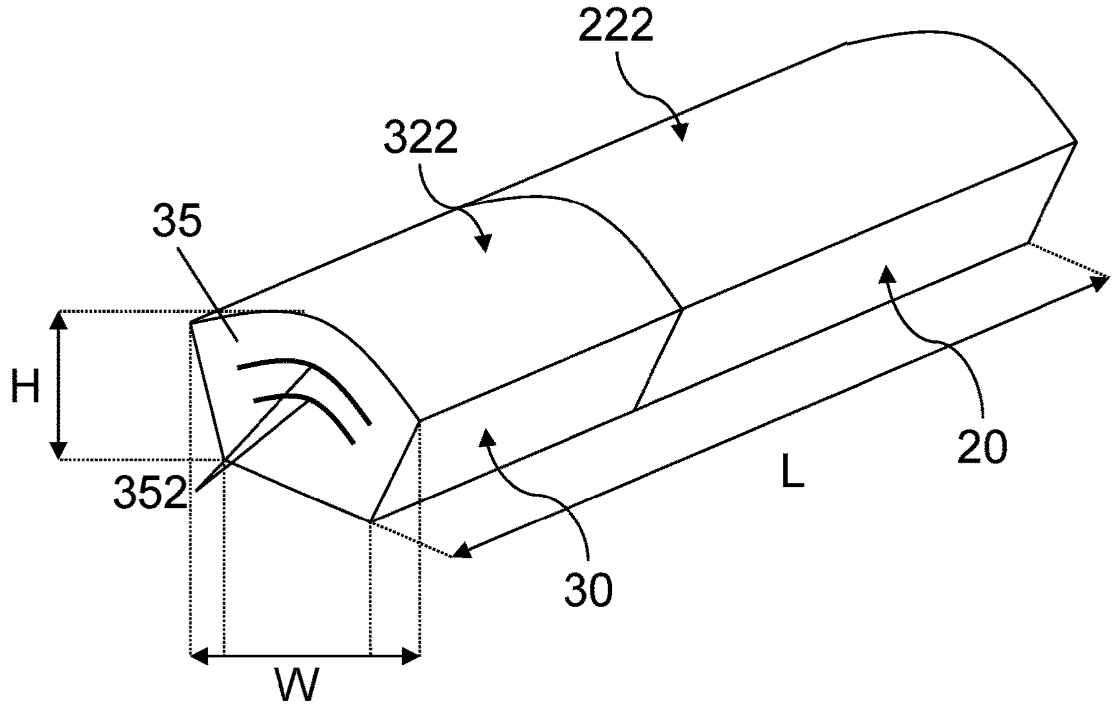
FIG. 4 schematically represents the aerosol delivery device of FIG. 1 in perspective view showing the outer surfaces thereof.

FIG. 4 is a schematic perspective view of the aerosol delivery device 10 of FIGS. 1 to 3 when the cartomizer 30 and control unit 20 are coupled together. In this implementation, the aerosol delivery device 10 is generally cuboidal and has a generally trapezoidal cross-section when viewed in a plane perpendicular to the longitudinal axis LA, wherein the longest side of the trapezium is curved between the two non-parallel sides of the trapezium. The separation distance between the two non-parallel sides is referred to herein as the width W of the aerosol delivery device 10 and increases in a direction from the lower surface 324 to the upper surface 322. The terms longest side and shortest side refer to the relative length of the sides taken in the width direction. FIG. 4 also shows the height H of the device which is the maximum separation distance between the longest, curved side and the shortest side, in addition to the length L, which is the total length of the aerosol delivery device 10 (i.e., cartomizer 30 and control unit 20 combined). The length direction is parallel to the longitudinal axis LA.

Accordingly, the upper surfaces 222 and 322 are curved in a width direction along the length of the aerosol delivery device 10. The cartomizer 30 and control unit 20 have the same cross-section along the longitudinal axis LA so that the respective upper and lower surfaces 222, 322; 224, 324 are contiguous with one another when the cartomizer 30 and control unit 20 are coupled together. The curved upper surfaces 222 and 322 provide a device that some users may find easier to grip/hold.

FIG. 4 also shows the two mouthpiece openings 352 at the mouthpiece end of the cartomizer 30. These openings 352 communicate with air flow channels provided throughout the aerosol delivery device 10 to allow air to be inhaled from outside the aerosol delivery device 10, through the device 10 to mix with the vaporized aerosol precursor material, and out through the openings 352 of the mouthpiece end 35 into the user's lungs. The openings 352 are provided in a crescent-shape wherein the upper opening is longer in length than the lower opening. It should be appreciated that this is one exemplary way of arranging the openings 352 and other arrangements of openings may be provided, such as a number of circular holes disposed in a predefined pattern or a single opening. In some implementations, the openings are arranged to provide a certain directionality to the air exiting the device. For example, the openings may be configured to direct air along a direction inclined with respect to the longitudinal axis.

Figure 5A:
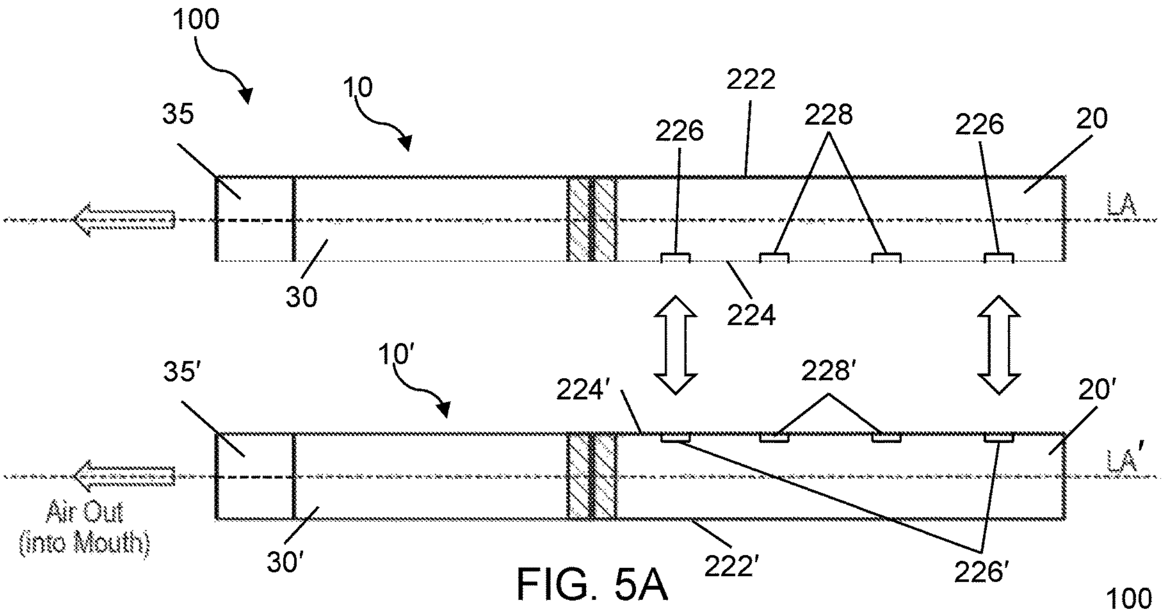
FIG. 5A schematically represents an aerosol delivery system comprising the aerosol delivery device of FIG. 1 and a second aerosol delivery device, both shown in cross-section along respective longitudinal axes thereof in an uncoupled state.
Figure 5B:
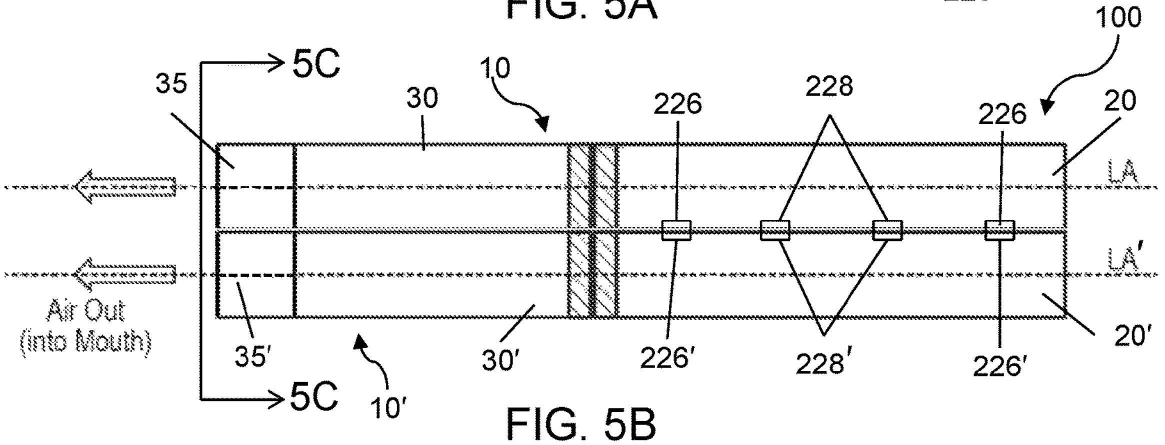
FIG. 5B schematically represents the aerosol delivery system of FIG. 5A in a releasably magnetically coupled state.

FIGS. 5A and 5B schematically show an aerosol delivery system 100 in accordance with some embodiments of the present disclosure. FIG. 5A schematically shows the aerosol delivery system 100 in an uncoupled/decoupled state while FIG. 5B schematically shows the aerosol delivery system 100 in a coupled state.

Referring to FIG. 5A first, the aerosol delivery system 100 of the present disclosure includes a plurality of aerosol delivery devices in an uncoupled state and shown having a separation distance between the delivery devices. The principles of this disclosure will be described herein with reference to two aerosol delivery devices but it should be appreciated the principles can equally be applied to an aerosol delivery system comprising more than two aerosol delivery devices.

FIG. 5A shows a first aerosol delivery device 10 which is the aerosol delivery device 10 of FIGS. 1 to 4. The cartomizer 30 and control unit 20 are coupled together by the connectors 25A and 25B and are provided in a state ready to generate and deliver aerosol to a user. In this state, a user can inhale on mouthpiece end 35 and receive aerosol generated by the aerosol delivery device 10 as described above.

In addition, FIG. 5A shows a second aerosol delivery device 10'. The second aerosol delivery device 10', in this implementation, includes similar components to the first aerosol delivery device 10. Components of the second aerosol delivery device 10' will be distinguished from those of the first aerosol delivery device 10 by use of a prime ('). Accordingly, for reasons of brevity, components having like reference signs but differing only by the presence of a prime have the same function and construction as the un-primed component previously described, unless described to the contrary. Therefore, the second aerosol delivery device 10' comprises a second cartomizer 30' including a second mouthpiece end 35' and a second control unit 20'. The second cartomizer 30' and second control unit 20' are coupled together by connections 25A' and 25B' and are provided in a state ready to generate and deliver aerosol to a user. In this state, a user can inhale on the second mouthpiece end 35' and receive aerosol generated by the second aerosol delivery device 10' as described in a similar manner with respect to the first aerosol delivery device 10.

The second cartomizer 30' may, optionally, differ from the cartomizer 30 by comprising a different source liquid in its reservoir 160' having, for example, a different flavor or a different strength/concentration of nicotine. Otherwise, in this implementation, the second cartomizer 30' is identical to the cartomizer 30.

The second control unit 20' differs in construction from the control unit 20 by the second engagement mechanism; specifically, in the orientation/alignment of the magnetic portions 226'. In this implementation, the magnetic portions 226' are arranged to have the polarity of each magnetic portion 226' reversed compared to the polarity of magnetic portions 226 of the first aerosol delivery device 10 to allow for a magnetic coupling between magnetic portions 226 of the first aerosol delivery device 10 and magnetic portions 226' of the second aerosol delivery device 10'. FIG. 5A shows two double-headed arrows indicative of the magnetic forces acting between the magnetic portions 226 and 226' of the respective aerosol delivery devices 10, 10'. As should readily be understood by one skilled in the art, when the magnetic poles of the magnetic portions 226' of the second aerosol delivery device 10' are reversed with respect to the corresponding magnetic portions 226 of the first aerosol delivery device 10, an attractive magnetic force is generated causing the magnetic portions 226 and 226' to be attracted to one another.

Accordingly, when the magnetic force is sufficiently strong, the aerosol delivery devices 10, 10' are forced towards one another by the attractive magnetic force and couple together. FIG. 5B shows the first and second aerosol delivery devices 10, 10' in a magnetically coupled state. In this state, the mouthpiece ends 35 and 35' of each aerosol delivery device 10, 10' are provided adjacent one another. In this regard, the magnetic force of coupling should be strong enough to not cause sliding/twisting/slipping of one aerosol delivery device relative to another during normal use (i.e., when inhaling on the devices), but should be sufficiently weak to enable a user to separate the devices 10, 10' by applying a force, or component thereof, in the direction in which the force of magnetic attraction acts. Hence, when coupled, a user can manipulate the two devices 10, 10' as though they were handling a single device without the devices 10, 10' becoming separated.

When coupled, the longitudinal axes LA, LA' of the respective aerosol delivery devices 10, 10' are substantially parallel as can be seen in FIG. 5B. Equally, because of the positioning of the magnetic portions 226 and 226', the aerosol delivery devices 10, 10' are provided such that the lengths thereof overlap/align. In other words, the overall length of the aerosol delivery system 100 from an edge of the first or second aerosol delivery device 10, 10' furthest in one direction along the longitudinal axis to an opposite edge furthest in the opposite direction along the longitudinal axis is approximately the same as the length of an individual aerosol delivery device 10, 10', barring any minor misalignments.

Figure 5C:
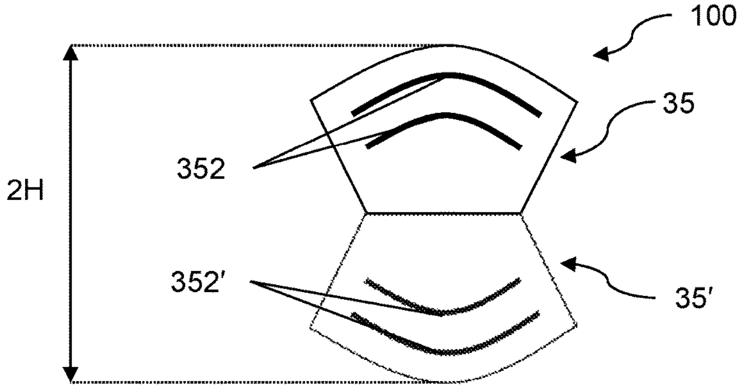
FIG. 5C schematically shows the aerosol delivery system of FIG. 5B as viewed along a longitudinal axis in a direction towards the mouthpieces/mouthpiece ends of the releasably magnetically coupled aerosol delivery devices.

FIG. 5C schematically represents the aerosol delivery system 100 in a coupled state (i.e., of FIG. 5B) when viewed along the longitudinal axis LA in a direction towards the mouthpiece ends 35, 35' as shown by line 5C in FIG. 5B. As can be seen, the lower surfaces 224, 324 and 224', 324' of each aerosol delivery device 10, 10' abut in the coupled state (and hence, relatively speaking, the lower surfaces 224' and 324' are actually the uppermost surfaces of the second aerosol delivery device 10'). In a coupled state, a user places their lips on the upper surface 322 of the first aerosol delivery device 10 (specifically an upper lip) and on the upper surface 322' of the second aerosol delivery device 10' (specifically a lower lip) to engage with the adjacent mouthpiece ends 35 and 35' simultaneously. In this way, when a user inhales on the aerosol delivery system 100 in a coupled state, a mixture of air is inhaled including air that passes through the first aerosol delivery device 10 (and which may include aerosol generated by the first aerosol delivery device) and air that passes through the second aerosol delivery device 10' (and which may include aerosol generated by the second aerosol delivery device). Air (which may include the generated aerosol) exits the respective aerosol delivery devices via the openings 352 and 352' as shown in FIG. 5C. Thus, a user can inhale a mixture of aerosol generated by both aerosol delivery devices 10, 10'.

The total height of the aerosol delivery system 100 is equal to twice the height H of the individual aerosol delivery devices 10, 10' as indicated in FIG. 5C. Therefore, the height H for each individual device 10, 10' should be chosen to provide a comfortable total height in the coupled state for a user to engage with both mouthpiece ends. By way of example only, the total height may be on the order of 15 mm meaning that each individual aerosol delivery device has a height H of 7.5 mm. This ensures the user is able to engage with both mouthpieces 35, 35' in a coupled state and each mouthpiece end separately in an uncoupled state.

It should be understood that in the coupled state each of the aerosol delivery devices 10, 10' can be operated to generate aerosol from the respective source liquids contained therein. The single user can thus inhale a mixture of both aerosols when the two devices are co-engaged/coupled. To change the respective aerosol combination (i.e., flavors/strengths) a user disconnects/decouples the first and second aerosol delivery devices 10, 10' and exchanges the second aerosol delivery device 10' for a third aerosol delivery device (not shown) having a different source liquid contained therein. Such changing of aerosol combinations does not require any significant disassembly of the individual aerosol delivery devices 10, 10'. Instead, the user can intuitively and easily swap aerosol sources by changing entire aerosol delivery devices without disconnecting individual cartomizers of the respective aerosol delivery devices.

Additionally, when the first and second aerosol delivery devices 10, 10' are magnetically coupled, the electrical contacts 228 and 228' of each aerosol delivery device 10, 10' are brought into contact to electrically couple/connect the control unit 20 with the control unit 20'. In a similar way to the magnetic portions 226 and 226', the control unit 20 may differ in construction from the control unit 20 in that the polarities of the electrical contacts 228' of the second aerosol delivery device 10' are reversed with respect to the polarities corresponding electrical contacts 228 on the first aerosol delivery device 10. This enables an appropriate electrical connection when the first and second aerosol delivery devices 10, 10' are magnetically coupled together. As described above, the electrical connection enables power and/or control signals to be passed between the first and second aerosol delivery devices 10, 10'.

The control signals are electrical signals that are received at either of the controllers located in the aerosol delivery devices and are used to determine how the respective aerosol delivery devices 10, 10' should operate.

Control signals include, for example, an indication of the volume or amount of aerosol to be generated for each of the respective aerosol delivery devices 10, 10' upon inhalation by a user. In this example, each of the controllers of the delivery devices 10, 10' are provided with source identification information which identifies the source liquid (more generally, the aerosol precursor material) contained in the respective aerosol delivery devices 10, 10'. For example, the first aerosol delivery device 10 may have a source liquid having an apple flavoring while the second aerosol delivery device 10' may have a source liquid having a strawberry flavoring. The source identification information can be programmed into the control unit 20, 20' of the respective delivery devices 10, 10' by a user prior to using the aerosol delivery devices 10, 10' e.g., through connecting to a computer or the like via a USB cable or, alternatively, each cartomizer 30, 30' is provided with an electronically readable chip or the like storing the source identification information and, when the cartomizers 30, 30' are coupled to their respective control units 20, 20', the chip is read by the controller to obtain the source identification information.

An optimal mixture of the flavors in the example given may be in the ratio of 2:1, for instance, as determined by the manufacturer of the cartomizers 30, 30' or as set by a user based upon their preferences. When the first and second aerosol delivery devices 10, 10' are first coupled, the source identification information is exchanged between the two devices using the electrical connection. Therefore, the first aerosol delivery device 10 receives an indication that it is to be mixed with a strawberry flavoring and, as a result, the controller controls the amount of power supplied to the heater 155 to generate a quantity of apple-flavored aerosol that is suitably mixed with the strawberry-flavored aerosol. This can be implemented based upon a look-up table referencing all produced flavors from the manufacturer and combinations thereof. Equally, the second aerosol delivery device 10' receives source identification information from the first aerosol delivery device 10' and correspondingly controls the heater 155' to generate a suitable quantity of strawberry-flavored aerosol in a similar manner. It should be appreciated that, in some implementations, the quantity of aerosol generated in respective aerosol delivery devices is also a function of the air flow flowing through the aerosol delivery device as detected, for example, using a suitable sensor. In these implementations, aerosol is generated in each device as a function of both the flavor ratio and the detected air flow such that, regardless of the strength of the air flow, the flavor ratio is maintained.

It should be appreciated that the above describes a situation whereby the volume of aerosol (and hence the ratio of flavors) is set automatically based upon the detected flavors to be combined and inhaled. In alternative implementations, a user may have direct control over the quantity of aerosol produced. As described above, a suitable sensor, such as a puff sensor is used to activate the heater 155, 155' when a puff is detected. To adjust the flavor ratio, the user may, for example, press on one or more buttons located on the upper surfaces 222 and 222' of the respective control units 20, 20' (not shown in the figures). Such buttons may allow dynamic changing of the ratio of flavors prior to or during inhalation (e.g., by increasing or decreasing the quantity produced by each individual aerosol delivery device 10, 10'). In some implementations, pressing a button on the first aerosol delivery device 10 may impact upon the aerosol generated by the second aerosol delivery device 10'. In this case, the control signals may include indications of button presses made on one of the aerosol delivery devices.

In other implementations, the user may perform some action that affects the air flow through one of the aerosol delivery devices when the devices are coupled. For example, the user may puff on only one of the mouthpiece ends (or more strongly on one end) or may block the openings of one mouthpiece end of the aerosol delivery device. The output from both puff sensors in these cases would be different and the difference can be attributed to certain control functions of the aerosol delivery device. For example, the aerosol delivery device having the larger airflow value as detected by the puff sensors may be controlled to increase the proportion of aerosol it generates in the mixture by increasing the relative power supplied to the heater, for example while decreasing the relative power supplied to the heater of the other aerosol delivery device. That is, if one aerosol delivery device is instructed to increase the volume of aerosol output (thus making the mixture more apple-based), the output of the other aerosol delivery device is decreased. A user can set the desired ratio based upon interacting with one or the other of the devices. The total volume of aerosol inhaled will depend upon the strength of the puff but the volume of each flavor inhaled is set relative to the total volume based upon the flavor ratio.

In other implementations, the control signals include communications between the controllers of the first and second aerosol delivery devices 10, 10', where said communications are used to establish a master controller responsible for controlling the functions of both the first and second aerosol delivery devices 10, 10'. Using a master controller may help reduce energy/power consumption because other controllers can be placed in a stand-by/lower-power mode. In addition, other components, e.g., flow/puff sensors, may also be placed in a low-power mode.

In this regard, when first coupled, the controllers are arranged to send device information (which may include the source identification information in addition to other parameters such as current battery charge, software/hardware version, usage statistics, etc.) to the other controller of the other aerosol delivery device. The controllers are programmed to determine, from the available controllers, a single controller (master controller) by comparing the received device information to their own device information. Each controller then determines whether or not it should be a master controller. If it is decided that a first controller should not be a master (e.g., because the battery charge is low compared to other devices, or the controller is not compatible with the other controller(s), or for some other reason) then no further action is taken.

Conversely, if the first controller determines that it should be a master controller, it transmits a signal (via the electrical connection) indicating its eligibility to the remaining controllers. If the remaining controllers do not consider themselves master controller candidates then the remaining controllers send an acknowledgement (ACK) signal back to the controller. If the total number of ACK signals is equal to the total number of sets of device information received, the controller then appoints itself master controller and assumes responsibility for each of the controllers (and hence the functions of each of the aerosol delivery devices 10, 10'). Conversely, if one of the remaining controllers determines that it is a candidate master controller, it transmits a negative acknowledgement (NACK) signal back to the first controller. On receiving the NACK signal the first controller does not become a master controller, and the controller sending the NACK signal remains a master controller candidate. The process can be cycled through until a master controller is selected or until the process is timed-out in which case a master controller may be selected at random from the candidate set.

It should be appreciated that the above is merely an example of how the master controller can be selected from a number of controllers. The exact process of how a master controller is selected is not particularly significant for the principles of the present disclosure, but rather that communications can occur between controllers of different aerosol delivery devices 10, 10' using the electrical connection. However, one skilled in the art will be aware of other processes which may be used in conjunction with or in place of the above described selection process for selecting the master controller.

In addition to control signals, the electrical contacts 228 and 228' also allow for power to be exchanged/transferred between aerosol delivery devices 10, 10'. In other words, electrical power from the battery or cell 210 of the first aerosol delivery device 10 can be transferred to the battery or cell 210' of the second aerosol delivery device 10' or directly to the heater 155' of the cartomizer 30' of the second aerosol delivery device 10'.

For example, electrical power can be shared between the first and second aerosol delivery devices 10, 10' to provide the respective batteries 210, 210' with the same level of charge. In other words, power can be supplied from the battery having the greatest charge to the battery having the lowest charge in order to charge the battery having the lowest charge. Power can be transferred from one battery to another until each of the batteries has equal or approximately equal charge so that, if decoupled, both aerosol delivery devices may be individually used to generate aerosol. In other implementations, the charge is distributed in proportion to the output ratio of aerosol; for instance, using the example above, power is distributed in a 2:1 ratio between first and second aerosol delivery devices 10, 10'.

In one implementation, the control units 20 and 20' are provided with appropriate circuitry configured to distribute power between the batteries in a passive manner—that is, as soon as the electrical connection is made using the contacts 228 and 228', power is transferred until the batteries reach an appropriate level of charge. Alternatively, the control units 20 and 20' are provided with circuitry configured to transfer power in response to certain actions. These certain actions may include, for example, a user pressing on a button provided on the upper surface 222 and/or 222' of the control unit 20 and/or 20' or in response to a detected puff/inhalation as detected by a suitable sensor.

In yet another alternative implementation, power is not supplied to the batteries 210 and 210' but is instead supplied directly to the heater 155 and/or 155' in response to a detected puff. For example, the controllers may determine which of the batteries has the greatest charge (based upon transmitting device information between the aerosol delivery devices 10, 10') and use the determined battery to supply power to both the heater 155 and heater 155' via the electrical connection. In this way, the battery having the greatest charge at any one time can preferentially be used to generate aerosol in both of the aerosol delivery devices 10, 10'. When the difference in charge reaches zero, or reverses (i.e., the battery supplying the power to both heater 155 and heater 155' becomes the battery with the lowest charge), then the battery responsible for supplying the power to both devices is switched and the other battery is used in its place. In this way, when the difference in charge between the batteries is small, the batteries are alternated between, meaning that at any one time the batteries have approximately the same level of charge. This provides similar benefits as described above.

In yet further implementations, each of the control units 20, 20' comprises a dedicated USB (or similar) charging port as described above. When coupled, a user may connect a USB power cable (i.e., a USB cable configured to supply power from a power source such as mains electricity) to either one of the USB charging ports. When a USB power cable is connected to a USB port, the electrical power supplied is distributed to the respective batteries 210, 210' using the electrical contacts 228, 228' so that both batteries may be charged using a single power cable and single port. For example, if a user connects the USB power cable to the control unit 20, the control unit 20 (or master controller) is configured to distribute some or all of the received power to the battery 210' of the control unit 20' via the electrical contacts 228 and 228'. The power may be transferred in accordance with any pre-set conditions. For example, the power may be distributed so that each battery receives half of the input power (i.e., 50% of the power is directed to battery 210 and 50% to battery 210'). Alternatively, the ratio of power distribution may be selected based upon the current level of charge of the batteries 210, 210' with the battery having the lower charge being distributed a larger proportion of the incoming power. In other implementations, the power is first distributed to the battery of the control unit coupled to the power cable, e.g., battery 210, to charge that battery to a certain level (e.g., fully charged) before being distributed to the battery of the control unit not coupled to the power cable, e.g., battery 210'. In this way, a user can sufficiently charge both (or multiple) aerosol delivery devices with only a single power cable and a single connection of the cable to the aerosol delivery system. This provides the user with a much simpler charging mechanism as the user only has to be concerned with connecting the cable to any of the charging ports.

An aerosol delivery system 100 in which two aerosol delivery devices 10, 10' are magnetically and electrically coupled together via respective engagement mechanisms co-engaging has been described above. In the described implementation, magnetic portions 226, 226' and electrical contacts 228, 228' are provided on one surface of the respective aerosol delivery devices. However, in other implementations, secondary (or further) magnetic portions and electrical contacts are disposed on other surfaces of the aerosol delivery devices. For example, the engagement mechanism of each aerosol delivery device is provided with two groups of magnetic portions and electrical contacts (disposed on the upper surfaces 222, 222' and the lower surfaces 224, 224'). In this implementation, each of the magnetic portions on the upper surfaces 222, 222' have their poles aligned in the same first direction, while each of the magnetic portions on the lower surfaces 224, 224' have their magnetic poles aligned in a second, opposite direction. Accordingly, such an arrangement facilitates the magnetic coupling of the upper and lower surfaces of respective aerosol delivery devices. Thus, unlike the described implementation above, if magnetic coupling is not permitted between two surfaces (because the magnetic portions 226, 226' repel each other), then in this implementation a user can rotate one aerosol delivery device by 180° about the longitudinal axis LA to provide a magnetic attraction between the secondary magnetic portions. Equally, the same can be said for the electrical contacts.

Moreover, in a further implementation, the engagement mechanisms (i.e., the magnetic portions) and the electrical contacts are disposed on the surfaces corresponding to the non-parallel sides of the generally trapezoidal cross-section of the aerosol delivery device in FIG. 4 (i.e., the sides connecting the upper and lower surfaces 222, 222' and 224, 224'). This arrangement can facilitate the magnetic coupling of many aerosol delivery devices in a ring-type arrangement by disposing aerosol delivery devices such that their non-parallel surfaces abut.

Although the magnetic portions 226, 226' of the engagement mechanisms and electrical contacts 228, 228' have been described as being provided on/in on/in surfaces of the control unit 20, 20', it should be understood that the engagement mechanisms (magnetic portions 226, 226') and/or electrical contacts 228, 228' may additionally or alternatively be provided on surfaces of the cartomizers 30, 30'.

Furthermore, in alternative implementations, the engagement mechanism of the second aerosol delivery device 10' comprises the housing of the control unit 20' or cartomizer 30'. In this implementation, the second aerosol delivery device is made of a magnetic material—that is, the housing of the control unit 20' is formed from a material that is magnetically attracted to the engagement mechanism of the first aerosol delivery device 10 (e.g., magnetic portions 226). Precise aligning of the magnetic portions 226 and 226' is therefore not required in this implementation and it is irrelevant whether or not magnetic portions on opposing devices are aligned in a manner to provide attractive magnetic coupling therebetween as in FIG. 5A. Instead, magnetic coupling occurs between the magnetic portions 226 and an area of the control unit 20'. Although in this implementation it is not required that both aerosol delivery devices 10, 10' are provided with the magnetic portions 226, 226', in other implementations both aerosol delivery devices 10, 10' are provided with their engagement mechanisms comprising both the magnetic portions 226 or 226' and the housing of the respective cartomizer 30, 30' and/or control unit 20, 20'. This can enable a stacked arrangement of aerosol delivery devices for example where coupling between two delivery devices of the stack is achieved by the magnetic portions of one aerosol delivery device coupling to the housing of the other delivery device as described above. It should be noted that the reservoirs 160, 160' may be constructed to contain any amount of aerosol precursor depending upon the application at hand. However, in one implementation, the total volume of liquid aerosol precursor material contained in each reservoir is set to, e.g., 2 ml divided by the number of aerosol delivery devices intended to be coupled together. Thus, for an aerosol delivery system consisting of two aerosol delivery devices, each reservoir is constructed to contain a maximum of 1 ml of liquid aerosol precursor. In this way, the total volume of liquid aerosol precursor material does not exceed 2 ml in normal use when the individual aerosol delivery devices are coupled.

Described above is an aerosol delivery system 100 comprising two aerosol delivery devices 10 and 10' that are magnetically coupled together. However, the principles of the present disclosure can be applied to aerosol delivery devices that comprise mechanical engagement mechanisms providing co-engagement of the aerosol delivery devices. That is, the aerosol delivery devices are selectively coupled together mechanically through the engagement mechanisms rather than magnetically.

Figure 6A:
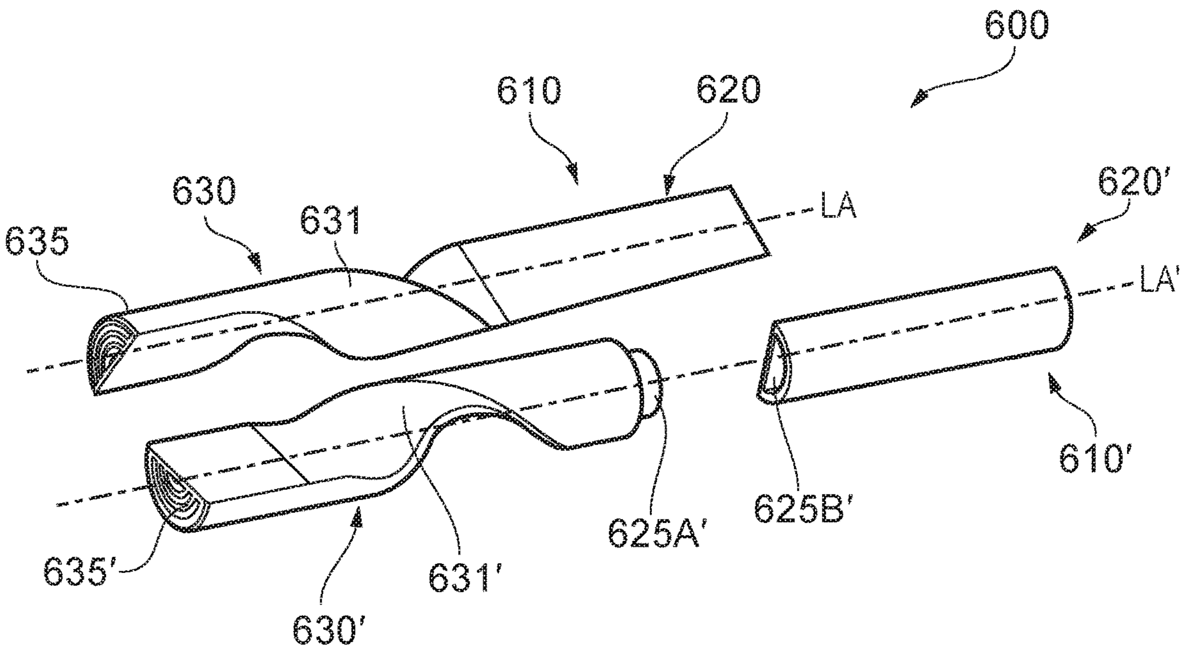
FIG. 6A shows an aerosol delivery system comprising two aerosol delivery devices in an uncoupled state in accordance with a second embodiment of the disclosure, each aerosol delivery device having an interlocking section configured to mechanically engage with a respective interlocking section.
Figure 6B:
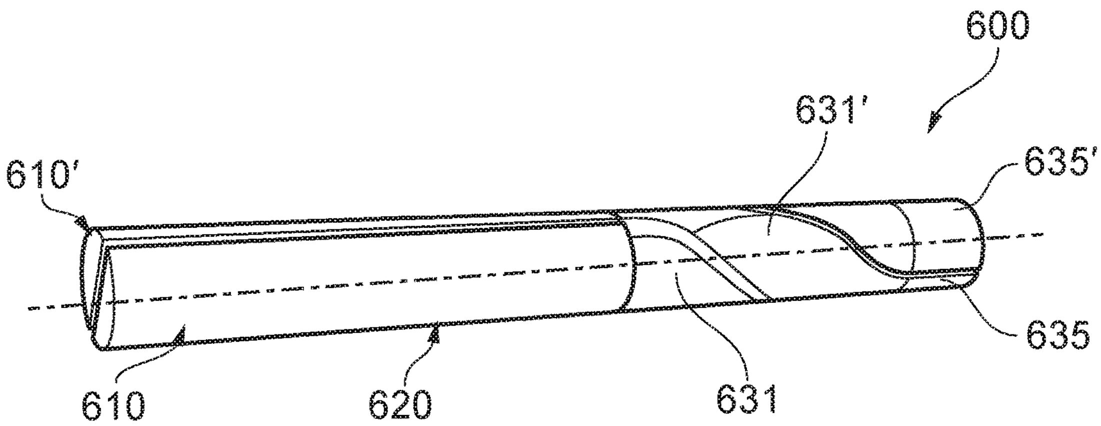
FIG. 6B shows the aerosol delivery system of FIG. 6A in a releasably mechanically coupled state.

FIGS. 6A and 6B schematically show two aerosol delivery devices 610 and 610' as viewed along a direction offset from the longitudinal axes thereof according to a second implementation of the present disclosure that, when coupled together, form a mechanically interlocked/coupled aerosol delivery system 600.

Specifically, FIG. 6A shows a first aerosol delivery device 610 and a second aerosol delivery device 610' in a decoupled state. The first and second aerosol delivery devices 610, 610' comprise respective cartomizers 630 and 630' and control units 620 and 620'. In FIG. 6A, the second control unit 620' is shown decoupled from the second cartomizer 630' and, as such, connectors 625A' and 625B' are exposed, while the first control unit 610 is shown coupled to the first cartomizer 630 via connectors (not shown).

The internal construction of the control units 620, 620' and the cartomizers 630, 630' is not shown in FIGS. 6A and 6B; rather, only the outer surfaces of the aerosol delivery devices 610, 610' are shown. However, the first and second aerosol delivery devices 610 and 610' comprise the necessary internal components required to function as an aerosol delivery device, e.g., components similar to those shown in FIGS. 2 and 3 with respect to the cartomizer 30 and control unit 20. The skilled person would readily employ the necessary components as required in view of the implementation described above and in accordance with conventional approaches.

The aerosol delivery devices 610, 610' in the second implementation generally have a hemi-cylindrical shape; that is, the cross-section at either end of the aerosol delivery devices 10, 10' is semi-circular. However, instead of the control units 620, 620' having magnetic portions to provide magnetic coupling as in the first implementation of FIGS. 1 and 5A to 5C, the aerosol delivery devices 610, 610' (specifically a section of the cartomizers 630, 630' thereof) are provided with interlocking sections 631, 631'. The interlocking sections constitute the respective engagement mechanisms of this implementation.

Each interlocking section 631, 631' is defined, in this implementation, from the end of the mouthpiece end 635, 635' joined to the interlocking section 631, 631' to the opposite end of the cartomizer 630, 630'. The interlocking section 631, 631' is formed from a transparent material to enable a user to see inside the cartomizer 630, 630'. The interlocking section 631, 631' is a hollow structure and includes a reservoir for each aerosol delivery device in this implementation in which the aerosol precursor material/liquid formulation is stored. Owing to the transparent construction, a user can visually detect when the aerosol precursor is running low or requires replacement. However, the aerosol delivery devices 610, 610' may generally be formed from any suitable materials, e.g., opaque plastic, metal, etc.

As can be seen in FIG. 6A, the interlocking sections 631, 631' are constructed in a manner such that the hemi-cylindrical shape progressively rotates about the longitudinal axis LA when moving along the respective longitudinal axes LA, LA' by a constant amount. That is, for the first aerosol delivery device 610, as one passes from the mouthpiece end 635 towards the opposite end of the cartomizer 630, the hemi-cylindrical shape rotates, e.g., clockwise, about the longitudinal axis LA by a total of approximately 270°. By way of example only, the hemi-cylindrical shape may be rotated clockwise by a constant amount of 54° per cm, thus meaning the interlocking section is approximately 5 cm in length (along the longitudinal axis). Similarly, the cartomizer 630' of the second aerosol delivery device 610' has a hemi-cylindrical shape that rotates at the same pitch as cartomizer 630 along the longitudinal axis LA' in the interlocking section 631'. In both interlocking sections 631, 631' shown in FIG. 6A, it should be appreciated that the semi-circular cross-section at the start of the interlocking section (i.e., the ends directly after the mouthpiece ends 635, 635') is offset relative to the semi-circular cross-section at the opposite end by 270° or 90° depending upon the definition of the direction of rotation about the longitudinal axis.

It should be appreciated, however, that in other implementations the extent to which the hemi-cylindrical cross-sectional shape is rotated along the longitudinal axis of the cartomizer 630, 630' may be more or less than that described above. For example, in one implementation, the hemi-cylindrical shape is rotated by a total of 90° about the longitudinal axis LA, LA' when moving from one end of the interlocking section along the longitudinal axis to the other end. That is, in this example, the hemi-cylindrical shape is rotated at a constant amount of 18° per cm over a length of 5 cm. In addition, in other implementations, the degree of rotation is not constant along the length of the interlocking section—for example, the rotation amount may vary along the length of the longitudinal axis LA, LA'. However, in the case of a varying rotation amount, the interlocking sections 631, 631' should be provided with the same or a similar degree/magnitude of variation at each position along the longitudinal axis.

This construction of the interlocking sections 631, 631' enables a user to couple together the aerosol delivery devices 610, 610' using a mechanical coupling. FIG. 6B schematically shows the aerosol delivery system 600 in a (releasably) coupled state whereby the user has performed a certain action to enable the aerosol delivery devices 610, 610' to mechanically couple.

In this implementation, the specific action involves aligning the interlocking sections 631, 631' of the respective aerosol delivery devices 610, 610' and twisting/pressing the interlocking sections 631, 631' together such that the flat surfaces of the hemi-cylindrical shapes of both aerosol delivery devices 610, 610' abut. FIG. 6B schematically shows the aerosol delivery system 600 in a (mechanically) coupled state, whereby the first and second aerosol delivery devices 610, 610' of FIG. 6A have been manipulated such that the interlocking portions 631, 631' interlock. As can be seen in FIG. 6B, when the separate aerosol delivery devices 610, 610' are interlocked, they define a cylindrical shape (composed of the respective hemi-cylindrical shapes) and share a common longitudinal axis. When coupled, the hemi-cylindrical shapes of the interlocking sections 631, 631' of this implementation are rotated in the same direction along the common longitudinal axis (e.g., clockwise) but the starting positions are offset from one another by 180°. Moreover, the interlocking sections 631, 631' enable the mouthpiece ends 635, 635' of the respective aerosol delivery devices 610, 610' to be provided adjacent one another when the devices 610, 610' are coupled.

The construction of the interlocking sections 631, 631' enables the interlocking sections (and thus the cartomizers 630, 630' and attached control units 620, 620') to be mechanically coupled together and held in a way such that only a specific set of actions will separate/uncouple the interlocking sections 630, 631'. Therefore, the interlocking sections 631, 631' prevent or substantially prevent sliding/twisting/slipping of one aerosol delivery device relative to another during normal use (i.e., when inhaling on the devices), but enable quick and intuitive separation of the aerosol delivery devices 610, 610' under application of the appropriate force/movement.

Although not shown, the interlocking sections 631, 631' are formed with a dividing wall running along the length of the respective interlocking sections to define two compartments within the hollow interior of the interlocking sections. In cross-section, the dividing wall divides the cross-section of the interlocking portions. The two compartments are fluidly isolated within the interlocking section. One of the compartments forms the reservoir and contains the aerosol precursor (e.g., the fluid to be vaporized). The other compartment forms an air passage, e.g., similar to air passage 161, to allow air to be passed from the control unit 620, 620' to the mouthpiece end 635, 635'.

In some implementations, the dividing wall is semi-circular in shape and, when viewed in cross-section, splits the semi-circular shape of the interlocking section into a first compartment having a semi-circular shape with a smaller radius than the overall semi-circular shape of the interlocking section, and a second compartment having an annular cross-section with a radius greater than the first compartment. In other words, the second compartment is formed to surround the outer curved edge of the first compartment, although it should be appreciated that the compartments can be formed to have other cross-sectional shapes. In this implementation, the dividing wall is twisted in accordance with the rotation of the respective interlocking section.

In the releasably coupled state, as with the aerosol delivery system 100, the mouthpiece ends 635, 635' of the respective aerosol delivery devices 610, 610' are adjacent one another. Equally, the respective longitudinal axes LA, LA' of the first and second aerosol delivery devices 610, 610' are provided parallel to one another. In much the same way as described for system 100, a user can place their lips around the respective mouthpiece ends 635, 635' to engage both mouthpiece ends simultaneously. When a user inhales on the mouthpiece ends 635, 635', air passes along the air passage (second compartment) of the respective interlocking sections (either prior to or after being mixed with the generated aerosol for the respective aerosol delivery devices 610, 610' depending upon the location of the heater) and into the mouthpiece end 635, 635'. As a result, a user inhaling on the mouthpiece ends 635, 635' can be provided with a mixture of aerosols generated by both the first and second aerosol delivery devices 610, 610'. It should be readily understood that, as with the aerosol system 100 described above, the aerosol system 600 permits users to intuitively and easily switch liquid formulations (e.g., flavors) without disassembling and reassembling the aerosol delivery devices 610, 610'. Additionally, each of the aerosol delivery devices 610, 610' is able to function independently in the decoupled state; that is, a user may inhale aerosol generated by device 610 when not coupled to device 610'.

It should be understood that interlocking section 631 is able to be mechanically interlocked with interlocking section 631' because the rotation of the hemi-cylindrical shapes are in the same directions about the longitudinal axes. Interlocking section 631 would not be able to interlock with another interlocking section having the same shape but rotated in the opposite direction about its longitudinal axis (e.g., anticlockwise by a constant amount of 54° per cm) in this implementation. Therefore, in much the same way as with the magnetic portions 226 and 226', certain interlocking sections (and thus cartomizers/control units) cannot be combined. This may also be the case where the rotation about the longitudinal axis is in the same direction but the variation in rotation degree along the longitudinal axes of the respective interlocking sections is different. This may be useful in preventing certain flavors flavours or nicotine strengths, for example, from being combined as these liquid formulations can be stored in mutually exclusive interlocking sections.

Although not shown in FIGS. 6A and 6B, the aerosol delivery devices 610, 610' may also be provided with electrical contacts, similar to electrical contacts 228, 228' to permit control signals or power to be transferred between coupled aerosol delivery devices 610, 610'. For example, the electrical contacts may be disposed on the flat (i.e., noncurved) surface of the hemi-cylindrical control units 620, 620'. Hence, when performing the interlocking motion, the electrical contacts are bought into contact to electrically couple the two aerosol delivery devices 610, 610'. The transfer of power and/or control signals may be carried out as described above.

The interlocking sections 631, 631' described above are merely given as an example and it will be appreciated by the skilled person that the interlocking sections 631 and 631' can take other shapes to provide a mutually interlocking function. For instance, the degree of rotation of the hemi-cylindrical shape may be more or less than described, or the general cross-section may be square or, more generally, polygonal in the interlocking sections as opposed to hemi-cylindrical. Equally, although the interlocking portions 631, 631' are shown as being formed in the cartomizers 630, 630', it should be understood that the control units 620, 620' may alternatively or additionally comprise the interlocking sections.

The above described second implementation makes use of the shape of the interlocking sections/cartomizers to provide a mechanical coupling. The engagement mechanisms by which the mechanical coupling occurs are therefore integrally formed with the aerosol delivery devices. In other implementations, the mechanical coupling of two or more aerosol delivery devices is achieved in other ways using an integrally formed mechanical coupling.

For example, although not shown, the aerosol delivery devices may integrally comprise one or more clips positioned on an outer surface thereof and configured to receive a portion of the other aerosol delivery device. The engagement mechanism of the first aerosol delivery device in this implementation is the one or more clips integrally formed with the outer surface thereof, while the engagement mechanism of the second aerosol delivery device is a section or part of the outer surface of the second aerosol delivery device that can be received by the one or more clips. For example, for a second aerosol delivery device having a circular or approximately circular cross-section, the clip is provided in a C-shape whereby the body of the second aerosol delivery device can be pressed into the inner part of the C-shape clip through the separation between the ends of the C. In this implementation, the C-shape clip is resiliently deformable and has an internal diameter/dimension slightly less (e.g. less than 10%, or less than 5%) than the diameter/dimension of the opposing aerosol delivery device. Accordingly, the resiliently deformable C-shape clip applies a radially compressive force on the opposing aerosol delivery device when located in the internal region of the C-shaped clip. Here, radially compressive force means a force acting towards the central point of the internal region of the C-shaped clip along a diameter thereof. Therefore, in this implementation, the two aerosol delivery devices can be mechanically coupled to provide a non-slipping/sliding arrangement during normal use. It should be apparent that the aerosol delivery devices can be coupled such that the mouthpiece ends thereof generally align as described above.

In alternative implementations, one aerosol delivery device may be provided with an integrally formed protrusion as the first engagement mechanism on an outer surface thereof which is shaped in a manner to be mechanically received (and held) in a correspondingly shaped recess provided on an outer surface of the other aerosol delivery device as the second engagement mechanism. Accordingly, by inserting the protrusion into the recess, and optionally sliding/rotating/pressing the protrusion into the recess (which may define a track along which the protrusion is guided during coupling), the two aerosol delivery devices can be mechanically coupled and held together during normal use. The protrusion and recess may take any corresponding shape that enables the two devices to be releasably locked together, e.g., corresponding T-shapes when viewed in cross-section. Such mechanical coupling mechanisms are generally known in the art and any suitable mechanism may be used in accordance with the principles of the present disclosure.

Additionally, the principles of the present disclosure do not require a specific mechanical coupling mechanism to be used. Any available mechanism that would be suitable may be used.

It has been described above that system 100 comprises aerosol delivery devices having a generally cuboidal shape, while system 600 comprises aerosol delivery devices have a generally hemi-cylindrical shape 600. However, the principles of the present disclosure are not limited to aerosol delivery devices having the described shapes and aerosol delivery devices having any shape can be used, provided that coupling between surfaces thereof is permitted. Additionally, the aerosol delivery devices 10, 10' 610, 610' have been described generally as being a two-piece construction comprising separate but connectable cartomizers 30, 30', 630, 630' and control units 20, 20', 620, 620'. However, the principles of the present disclosure apply to aerosol delivery devices being formed of more or less than two main constituent components. For example, the disclosure applies to aerosol delivery devices having a single-piece (i.e., integrated) construction.

It has also generally been disclosed above that aerosols generated by each of the aerosol delivery devices are mixed and inhaled. That is, the air that the user inhales comprises a mixture of the different aerosols that is mixed upon exiting the mouthpiece end. However, in other implementations, the two aerosols may be substantially kept separate during inhalation by the user. In these implementations, the different generated aerosols are directed to different areas of the mouth using mouthpiece ends 35, 35' that impart directionality to the individual aerosols as described above. When the aerosol delivery devices are coupled, the different aerosols are directed along different directions. For example, the aerosol generated by a first device may be generally directed along a first direction angled with respect to the longitudinal axis LA, LA' while aerosol generated by a second device may be generally directed along a second direction angled with respect to the longitudinal axis but different from the first direction. Although the areas of the mouth that the aerosol is directed to will depend upon the orientation of the coupled aerosol delivery devices, one could imagine the different aerosols being separately directed to the left and right sides of the mouth cavity.

Thus, there has been described an aerosol delivery system including: a first engagement mechanism, a first power supply, and a first vaporizer, wherein the first vaporizer is arranged to selectively receive power from the first power supply to generate a first aerosol from a first aerosol precursor material for user inhalation; and a second aerosol delivery device comprising a second engagement mechanism, a second power supply, and a second vaporizer, wherein the second vaporizer is arranged to selectively receive power from the second power supply to generate a second aerosol from a second aerosol precursor material for user inhalation; wherein the first engagement mechanism of the first aerosol delivery device and the second engagement mechanism of the second aerosol delivery device are arranged to releasably co-engage with one another to selectively couple the first aerosol delivery device to the second aerosol delivery device so the first aerosol delivery device and the second aerosol delivery device may be used together to deliver the first and second aerosols to a single user when they are coupled together and may be used independently to deliver the first and second aerosols to different users when they are not coupled together.

While the above described embodiments have in some respects focused on some specific example aerosol delivery systems, it will be appreciated the same principles can be applied for aerosol delivery systems using other technologies. That is to say, the specific manner in which various aspects of the aerosol delivery system function are not directly relevant to the principles underlying the examples described herein.

In order to address various issues and advance the art, this disclosure shows by way of illustration various embodiments in which the claimed invention(s) may be practiced. The advantages and features of the disclosure are of a representative sample of embodiments only, and are not exhaustive and/or exclusive. They are presented only to assist in understanding and to teach the claimed invention(s). It is to be understood that advantages, embodiments, examples, functions, features, structures, and/or other aspects of the disclosure are not to be considered limitations on the disclosure as defined by the claims or limitations on equivalents to the claims, and that other embodiments may be utilized and modifications may be made without departing from the scope of the claims. Various embodiments may suitably comprise, consist of, or consist essentially of, various combinations of the disclosed elements, components, features, parts, steps, means, etc. other than those specifically described herein, and it will thus be appreciated that features of the dependent claims may be combined with features of the independent claims in combinations other than those explicitly set out in the claims. The disclosure may include other inventions not presently claimed, but which may be claimed in future.

The invention claimed is:

1. An aerosol delivery system comprising:

a first aerosol delivery device comprising a first engagement mechanism, a first power supply, and a first vaporizer, wherein the first vaporizer is arranged to selectively receive power from the first power supply to generate a first aerosol from a first aerosol precursor material for user inhalation; and a second aerosol delivery device comprising a second engagement mechanism, a second power supply, and a second vaporizer, wherein the second vaporizer is arranged to selectively receive power from the second power supply to generate a second aerosol from a second aerosol precursor material for user inhalation;

wherein the first engagement mechanism of the first aerosol delivery device and the second engagement mechanism of the second aerosol delivery device are arranged to releasably co-engage with one another to selectively couple the first aerosol delivery device to the second aerosol delivery device so the first aerosol delivery device and the second aerosol delivery device may be used together to deliver the first aerosol and the second aerosol to a single user when the first aerosol delivery device and the second aerosol delivery device are coupled together and may be used independently to deliver the first aerosol and the second aerosol to different users when the first aerosol delivery device and the second aerosol delivery device are not coupled together.

2. The aerosol delivery system of claim 1, wherein the first aerosol delivery device comprises a first mouthpiece opening through which the first aerosol is delivered to a user during use and the second aerosol delivery device comprises a second mouthpiece opening through which the second aerosol is delivered to a user during use, wherein the first mouthpiece opening and the second mouthpiece opening are arranged adjacent when the first aerosol delivery device and the second aerosol delivery device are coupled together.

3. The aerosol delivery system of claim 1, wherein the first aerosol delivery device and the second aerosol delivery device are elongate and extend along respective longitudinal axes which are parallel to one another when the first aerosol delivery device and the second aerosol delivery device are coupled together.

4. The aerosol delivery system of claim 1, wherein the first engagement mechanism and the second engagement mechanism comprise one or more magnets arranged to selectively magnetically couple the first aerosol delivery device to the second aerosol delivery device.

5. The aerosol delivery system of claim 1, wherein the first engagement mechanism and the second engagement mechanism comprise mechanically interlocking elements arranged to selectively mechanically couple the first aerosol delivery device to the second aerosol delivery device.

6. The aerosol delivery system claim 1, wherein the first engagement mechanism comprises a portion of the first aerosol delivery device having a first shape, and the second engagement mechanism comprises a portion of the second aerosol delivery device having a second shape, wherein the first shape is arranged to cooperatively engage with the second shape to selectively couple the first aerosol delivery device to the second aerosol delivery device.

7. The aerosol delivery system of claim 6, wherein the first shape and the second shape comprise interlocking spiral portions of the respective first aerosol delivery device and the second aerosol delivery device.

8. The aerosol delivery system of claim 6, wherein the first shape and the second shape are arranged so that the first aerosol delivery device is selectively mechanically coupled to the second aerosol delivery device by bringing the first aerosol delivery device and the second aerosol delivery device into contact with the respective axes of extent perpendicular to one another, and then rotating one of the first aerosol delivery device or the second aerosol delivery device relative to the other so the respective axes of extent become parallel to one another while also rotating at least one of the first aerosol delivery device or the second aerosol delivery device about the respective axis of extent.

9. The aerosol delivery system of claim 1, wherein the first engagement mechanism comprises a resilient clip and the second engagement mechanism comprises a portion of the second aerosol delivery device arranged to be engaged by the resilient clip to selectively couple the first aerosol delivery device to the second aerosol delivery device.

10. The aerosol delivery system claim 1, wherein the first engagement mechanism comprises a protrusion from the first aerosol delivery device and the second engagement mechanism comprises a recess in the second aerosol delivery device, wherein the recess in the second aerosol delivery device is arranged to receive the protrusion from the first aerosol delivery device to selectively couple the first aerosol delivery device to the second aerosol delivery device.

11. The aerosol delivery system of claim 1, wherein the first aerosol delivery device comprises a first electrical interface and the second aerosol delivery device comprises a second electrical interface, wherein the respective first electrical interface and the second electrical interface are arranged to provide an electrical connection between the first aerosol delivery device and the second aerosol delivery device when the first aerosol delivery device and the second aerosol delivery device are coupled together.

12. The aerosol delivery system of claim 11, wherein the first aerosol delivery device comprises a first control unit configured to control operation of the first aerosol delivery device, and the second aerosol delivery device comprises a second control unit configured to control the operation of the second aerosol delivery device, and wherein at least one of the first control unit or the second control unit is configured to control an aspect of operation of the other of the first aerosol delivery device or the second aerosol delivery device by control signaling exchanged via the electrical connection between the first aerosol delivery device and the second aerosol delivery device when the first aerosol delivery device and the second aerosol delivery device are coupled together.

13. The aerosol delivery system of claim 12, wherein the aspect of the operation of the other of the first aerosol delivery device or the second aerosol delivery device comprises an amount of power supplied to the vaporizer of the other of the first aerosol delivery device or the second aerosol delivery device.

14. The aerosol delivery system of claim 11, wherein, when the first aerosol delivery device and the second aerosol delivery device are coupled together, at least one of:

the first vaporizer is further arranged to selectively receive power from the second power supply via the electrical connection between the first aerosol delivery device and the second aerosol delivery device, or the second vaporizer is further arranged to selectively receive power from the first power supply via the electrical connection between the first aerosol delivery device and the second aerosol delivery device.

15. The aerosol delivery system of claim 14, wherein relative amounts of power supplied to one of the first vaporizer or the second vaporizer from the first power supply and the second power supply is determined based on relative amounts of power remaining in the first power supply and the second power supply.

16. An aerosol delivery device comprising:

a power supply;

a vaporizer arranged to selectively receive power from the power supply to generate an aerosol from an aerosol precursor material for user inhalation; and an engagement mechanism for releasably co-engaging the aerosol delivery device with a further aerosol delivery device arranged to generate a further aerosol for user inhalation so the aerosol delivery device and the further aerosol delivery device may be used together to deliver aerosol to a single user when the aerosol delivery device and the further aerosol delivery device are coupled together and the aerosol delivery device may be used independently of the further aerosol delivery device when the aerosol delivery device is not coupled to the further aerosol delivery device.

17. An aerosol delivery system comprising:

first aerosol delivery means comprising first engagement means, first power supply means, and first vaporizing means, wherein the first vaporizing means is arranged to selectively receive power from the first power supply means to generate a first aerosol from a first aerosol precursor material for user inhalation; and second aerosol delivery means comprising second engagement means, second power supply means, and second vaporizing means, wherein the second vaporizing means is arranged to selectively receive power from the second power supply means to generate a second aerosol from a second aerosol precursor material for user inhalation;

wherein the first engagement means of the first aerosol delivery means and the second engagement means of the second aerosol delivery means are arranged to releasably co-engage with one another to selectively couple the first aerosol delivery means to the second aerosol delivery means so the first aerosol delivery means and the second aerosol delivery means may be used together to deliver the first aerosol and the second aerosol to a single user when the first aerosol delivery means and the second aerosol delivery means are coupled together and may be used independently to deliver the first aerosol and the second aerosol to different users when the first aerosol delivery means and the second aerosol delivery means are not coupled together.

* * * * *